(12) United States Patent
Rulkens et al.

(10) Patent No.: US 9,128,493 B2
(45) Date of Patent: Sep. 8, 2015

(54) METHOD AND APPARATUS FOR PLATING SOLUTION ANALYSIS AND CONTROL

(75) Inventors: Ron Rulkens, Milpitas, CA (US);
Nanhai Li, Pleasanton, CA (US); Artur Kolics, Dublin, CA (US); Aman Jain, Cupertino, CA (US); Darin Birtwhistle, San Francisco, CA (US); Chee Chan, Cupertino, CA (US)

(73) Assignee: Lam Research Corporation, Fremont, CA (US)

( * ) Notice: Subject to any disclaimer, the term of this patent is extended or adjusted under 35 U.S.C. 154(b) by 542 days.

(21) Appl. No.: 12/333,893

(22) Filed: Dec. 12, 2008

(65) Prior Publication Data

US 2009/0157229 A1 Jun. 18, 2009

Related U.S. Application Data

(60) Provisional application No. 61/012,998, filed on Dec. 12, 2007.

(51) Int. Cl.
| | |
|---|---|
| *G01N 21/00* | (2006.01) |
| *G05D 11/13* | (2006.01) |
| *C25D 21/12* | (2006.01) |
| *C25D 21/14* | (2006.01) |
| *G01N 21/31* | (2006.01) |
| *G01N 21/65* | (2006.01) |

(Continued)

(52) U.S. Cl.
CPC ............... *G05D 11/138* (2013.01); *C25D 21/12* (2013.01); *C25D 21/14* (2013.01); *G01N 21/31* (2013.01); *G01N 21/65* (2013.01); *G01N 21/85* (2013.01); *G01N 2021/8416* (2013.01)

(58) Field of Classification Search
CPC ........ G01N 21/65; G01J 3/44; C23C 18/1657
USPC .......................................... 422/110; 205/794
See application file for complete search history.

(56) References Cited

U.S. PATENT DOCUMENTS

| | | |
|---|---|---|
| 4,096,301 A | 6/1978 | Slominski et al. |
| 4,774,101 A | 9/1988 | Harris et al. |

(Continued)

FOREIGN PATENT DOCUMENTS

| | | |
|---|---|---|
| CN | 1793854 A | 6/2006 |
| JP | H06-033249 A | 2/1994 |

(Continued)

OTHER PUBLICATIONS

Vojinovic et al. "Real-time bioprocess monitoring", Sensors and Actuators B: Chemical: International Journal Devoted to Research and Development of Physical and Chemical Transducers, ELSEVIER S.A, Apr. 26, 2006.

(Continued)

*Primary Examiner* — Natalia Levkovich
(74) *Attorney, Agent, or Firm* — Beyer Law Group LLP (57) ABSTRACT

A plating system comprises a plating solution and an apparatus for control of the plating solution, the apparatus including a Raman spectrometer for measurement of organic components, a visible light spectrometer for measurement of metallic components, and a pH probe. The plating solution can be sampled continuously or at intervals. Dosing of the plating solution adjusts for components consumed or lost in the plating process. The method of dosing is based on maintaining a desired composition of the plating solution.

20 Claims, 8 Drawing Sheets

(51) Int. Cl.
    *G01N 21/85* (2006.01)
    *G01N 21/84* (2006.01)

(56) References Cited

U.S. PATENT DOCUMENTS

| | | | |
|---|---|---|---|
| 2003/0049858 | A1 | 3/2003 | Golden et al. |
| 2004/0046121 | A1* | 3/2004 | Golden et al. ............ 250/339.07 |
| 2004/0218173 | A1* | 11/2004 | Fisher et al. .................. 356/300 |

FOREIGN PATENT DOCUMENTS

| | | |
|---|---|---|
| JP | 2003-247077 A | 9/2003 |
| JP | 2003-253453 A | 9/2003 |
| KR | 10-2003-0025424 | 3/2003 |
| KR | 100414550 B1 | 1/2004 |
| KR | 1020050091288 | 9/2005 |
| WO | WO-2009075885 A2 | 6/2009 |
| WO | WO-2009075885 A3 | 6/2009 |

OTHER PUBLICATIONS

Taiwan Office Action from TW application 097148577 mailed on Oct. 21, 2013.

European Supplementary Search Report in EPO application 08859699.4 mailed Mar. 18, 2014.

* cited by examiner

METHOD AND APPARATUS FOR PLATING SOLUTION ANALYSIS AND CONTROL

CROSS-REFERENCE TO RELATED APPLICATIONS

This application claims the benefit of U.S. Provisional Application Ser. No. 61/012,998 filed Dec. 12, 2007 and entitled "Method and Apparatus for Plating Solution Analysis and Control," the content of which is incorporated by reference herein in its entirety.

TECHNICAL FIELD

The present invention is related to the analysis and control of a plating solution. More specifically, the present invention provides an improved method and apparatus for analyzing both organic and metallic ion components in a plating solution and for adjusting the concentrations of those components to optimize the physical attributes of a plated film while achieving other useful objectives such as minimizing waste and chemical usage.

BACKGROUND ART

Copper films are increasingly employed in semiconductor devices as a replacement for aluminum in the fabrication of electrical conductors. Skilled artisans will appreciate that copper conductors have a variety of benefits including higher conductivity and reduced susceptibility to electromigration (which degrades device reliability). Nevertheless, the application of copper conductors includes certain drawbacks, one of which is a decreased adhesion to dielectric films which are employed to separate conducting paths within the semiconductor devices. The reduced adhesion of copper to certain dielectric materials can lead to new failure mechanisms which reduce the utility of copper conductors, especially as new dielectric materials are introduced in association with advanced semiconductor processing technology.

One method of mitigating the problems associated with copper conducting films is to coat the copper surface or surfaces with an additional material having higher adhesion to dielectric materials. One proposed technique involves the electroless plating of cobalt tungsten phosphide (CoWP) onto the copper film before application of a dielectric film. The electroless plating process involves placing a semiconductor device undergoing fabrication into a plating solution which selectively deposits the CoWP on exposed copper metal only, and does not require any masking steps or application of external electrical currents. The plating solution is a combination of organic and inorganic chemical components which interact to nucleate the desired film and cause its growth so as to produce desired physical and chemical properties such as composition, conductivity, thickness, and grain structure.

In one example of a plating solution for the electroless plating of CoWP, cobalt chloride or cobalt sulfate is employed as a source for cobalt ions, sodium tungstate is employed as a source for tungsten ions, and sodium hypophosphite is employed as a source for phosphorus-containing ions. The organic chemical dimethylamine borane (DMAB) is employed as a reducing agent for reducing the cobalt and tungsten ions. Typically, the DMAB initiates the metal alloy plating on the copper surface. After initiation, further reduction occurs partially by action of the DMAB and by hypophosphite ions, which also participate in the reactions. In conventional electroplating, metal ions in a plating solution receive electrons from an external power supply and are chemically reduced to metallic form. In electroless plating, the reducing electrons are supplied by the chemical reducing agent. A complexing agent such as citric acid may be employed to stabilize metal ions in solution and to reduce the possibility of spontaneous decomposition. Citric acid can further act as a pH adjuster.

During the deposition process, reactants in the plating solution are consumed and waste products may accumulate. In order to ensure that the plating solution constituents remain within desirable concentration levels it is necessary to measure and adjust the component concentrations. One approach, known to those skilled in the art, is to take a sample of the plating bath and perform conventional chemical titrations to determine the concentrations of the plating bath constituents. A disadvantage to this approach is that it is slow and tedious. Another disadvantage is that the titration results in a significant amount of waste generation and a need for supplying additional chemicals needed by the titration process. Finally, the titration process is typically conducted away from the process equipment performing the electroless plating process. Additionally, matrix effects may confound the titration process in which the presence of one chemical component inhibits or alters the quantitative determination of other components.

Articles in trade publications familiar to those skilled in the art have proposed methods for control of electroless plating baths. For example, a cyclic voltametric stripping (CVS) technique has been discussed as a method to analyze organic components in a cobalt tungsten phosphide (CoWP) electroless plating solution. Other articles have also suggested UV-vis spectroscopic techniques for a determination of the concentration of metal ions in a plating solution. Raman spectroscopy has also been given mention as potentially applicable to the monitoring of chemical solutions utilized in electroless plating. Skilled artisans will appreciate that effective utilization of these techniques for plating bath control would benefit from a detailed teaching of how these analytical techniques may be combined and configured.

Specifically, methods are needed for using quantitative results obtained from these systems for the real-time or near real-time control of the plating bath. Further, a means of measurement and control of the plating solution pH in combination with spectroscopic techniques would advance the art. Skilled artisans recognize that pH is a measure of the hydronium ion ($H_3O+$) concentration in solution; pH is approximately equal to $\log_{10}[H_3O+]$, where $[H_3O+]$ is the hydronium ion concentration in moles per liter of solution.

Therefore, what is needed is an improved means for measuring and controlling concentrations of chemical constituents in a plating bath. In particular, a system is needed which combines the capabilities of determining the concentrations of organic constituents and metals in the plating bath, as well as a measure of the pH of the plating bath with methods for altering the plating bath constituent concentrations so as to produce plated films having desirable physical and chemical properties. The measurements should be largely immune from matrix effects and should operate in a comparatively short time interval to enable real-time or near real-time control of the plating bath.

SUMMARY OF THE INVENTION

These needs have been met in the present invention which presents a method and an apparatus for sampling a plating bath by drawing a comparatively small amount of plating solution by means of a solution input manifold and conveying the solution to a flow cell having a Raman spectrometer and a visible light spectrometer (VIS). The sample is additionally conveyed to a pH probe. The Raman spectrometer is capable of simultaneous measurement of multiple organic components, and is used in a particular embodiment of the present invention for the determination of dimethylamine borane (DMAB) concentration in the plating solution. Additionally, the Raman spectrometer can be employed for the measurement of inorganic components such as hypophosphite, phosphite, borate, tungstate, and other ions responsive to the wavelength range of operation for the instrument. The visible light (VIS) spectrometer is used for determination of the metals concentration in solution. These ions may include, but are not limited to, copper, nickel, cobalt, iron, palladium, and platinum.

The pH probe measures hydronium ion concentration (pH) of the plating solution, and optionally incorporates a temperature sensor to enable correlations of the pH measurements with the plating bath temperature. A control system makes additions of any of a plurality reagent chemicals and deionized (DI) water to the plating solution on the basis of the measurements made by the Raman spectrometer, the VIS spectrometer, and the pH probe. The control system employs a method for adjusting dosing additions to maintain a proper plating solution composition and volume.

DETAILED DESCRIPTION OF THE INVENTION

Figure 1:
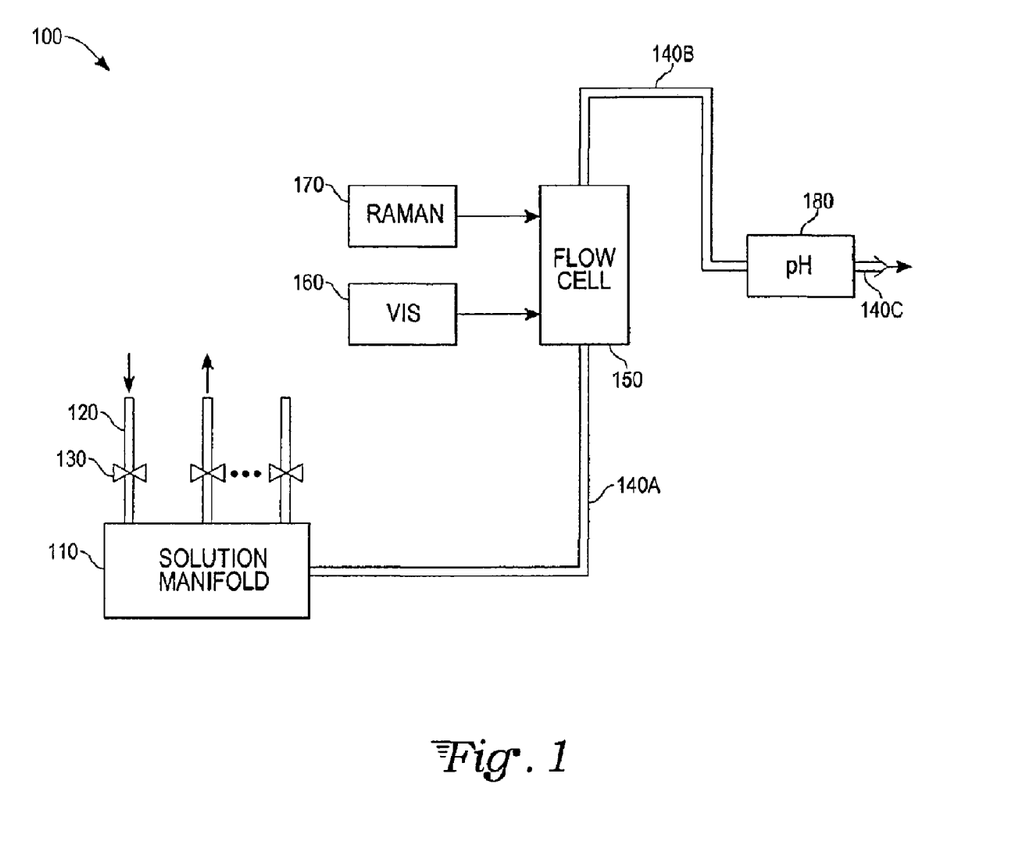
FIG. 1 is an apparatus for sampling a plating bath according to an exemplary embodiment of the present invention.

With reference to FIG. 1, an exemplary embodiment of the present invention comprises a solution sampling and control apparatus 100 including a solution manifold 110. A plurality of process solution tubes 120, each of which include a throttling valve 130 are coupled to the solution manifold 110. The process solution tubes 120 may each, in turn, be coupled to any of a plating bath having a plating solution, reagent chemical sources, and deionized (DI) water (not shown to avoid obscuring the present invention). The reagent chemical sources and deionized (DI) water are collectively referred to below as process chemicals.

In an exemplary embodiment of the present invention, the reagent chemical sources include dimethylamine borane (DMAB), citric acid, a solution of tetramethyl ammonium hydroxide (TMAH), and a solution containing cobalt ions, tungsten ions (i.e., a tungstate solution), and phosphorous-containing ions (e.g., hypophosphite). Skilled artisans will appreciate that a variety of plating solutions are available which contain various ions, alone or in combination. The discussions which follow are not intended to be limiting to a specific solution or combination of solutions. Those skilled artisans will recognize that other components, such as a pumping means (not shown), may be incorporated into the solution sampling and control apparatus 100 in order to enable circulation of process chemicals and the plating bath. The process solution tubes 120 may be used either for conveying process chemicals into or out of the solution manifold 110, as indicated by arrows in FIG. 1. The solution manifold 110 functions as means for introducing process chemicals into the plating bath and for drawing a sample of the plating solution from the plating bath for analysis, to be explained below. In this exemplary embodiment of the present invention, the plating bath volume is approximately 8 liters and the sample of the plating solution is approximately 20 milliliters.

A first sample tube 140A is used to convey a sample of the plating solution from the solution manifold 110 to a flow cell 150. A visible light spectrometer (VIS) 160 is coupled to the flow cell 150 and is responsive to the concentration of one or more metal ions in solution. The visible light spectrometer (VIS) 160 operates by light absorption, using techniques well known to those skilled in the art. In an exemplary embodiment of the present invention, the visible light spectrometer (VIS) 160 is a commercial instrument which utilizes a light emitting diode (LED) as a light source to measure absorbance in a specific wavelength range. The emission wavelength of the light emitting diode (LED) is in the green portion of the visible spectrum with a wavelength of range of between approximately 490 nanometers and 540 nanometers. Other embodiments of the present invention are possible which utilize spectrometers operating at other wavelengths, including wavelengths outside the visible range, in order to be responsive to a variety of different ions. Additionally, it is possible to use more than one spectrometer in the present invention, such that each spectrometer used is associated with a specific ion.

An advantage of the light emitting diode (LED) as a light source is greater optical output as compared with conventional (e.g., incandescent) sources, and longer lifetime and reliability, as well as a lower cost in comparison with laser sources. An important attribute of the light emitting diode is sufficient optical power to penetrate the plating solution. Skilled artisans will appreciate that solutions having different metal ions will vary in optical properties (in particular, absorbance versus wavelength) and that selection of different wavelength (i.e., different color) light sources for the visible light spectrometer (VIS) 160 will potentially benefit discrimination of the metal ion or ions of interest. The output of the measurements made by the visible light spectrometer (VIS) 160 is usually expressed in terms of absorbance. The absorbance (Abs) is related to the percentage of the spectrometer light source (the transmittance, % T) which passes through a solution sample and is given by the formula: Abs=$2\log_{10}$(%T) =$\log_{10}$(100/%T). Typically, a high value of absorbance (i.e., low transmittance) is associated with a high concentration of ions in solution.

A Raman spectrometer 170 is also coupled to the flow cell 150. In an exemplary embodiment of the present invention, the Raman spectrometer 170 has an optical source emitting at 785 nanometers. At this wavelength, the Raman spectrometer is responsive to the dimethylamine borane in the plating solution sample, and produces an output which is responsive to the concentration of the dimethylamine borane. Skilled artisans will appreciate that Raman spectroscopy operates in the infrared portion of the spectrum, where the interaction of infrared light with a chemical typically involves molecular vibrations. Because various organic molecules have different vibrational states, it is possible to distinguish between organic molecule types on the basis of wavelength versus response characteristics. Thus, Raman spectroscopy is responsive to a variety of organic chemicals, and the wavelength chosen for operation may be used to discriminate between organic chemicals even if a plurality of organic chemicals are present in a single sample.

The flow cell 150 construction may follow any number of techniques known to those skilled in the art. However, the construction in an exemplary embodiment of the present invention is chosen so as to minimize a volume of solution required to fill the cell. The small volume is advantageous to minimizing the production of chemical waste and to reduce the cost of chemicals potentially lost to the sampling process. An additional advantage is potentially faster sampling times by reduction of the amount of solution that must be pumped into the cell in order to obtain a representative sample of the plating bath.

A second sample tube 140B couples the flow cell 150 to a pH probe 180. The sample of the plating solution from the solution manifold 110 which was conveyed by the first sample tube 140A to the flow cell 150 is further conveyed by the second sample tube 140B to the pH probe 180 which provides a signal responsive to the hydronium ion concentration (pH) of the sample. A third sample tube 140C is coupled to the pH probe 180 and conveys the sample of the plating solution out of the pH probe. The sample may be discarded as waste or may be returned to the plating bath. Skilled artisans will recognize that the sample of the plating bath which is passed to the flow cell 150 and the pH probe 180 may be sent intermittently or continuously. Those skilled artisans will also appreciate that other configurations of the flow cell 150 and the pH probe 180 are possible. For example, the pH probe 180 may be configured to first measure the sample of the plating solution before the sample is passed to the flow cell 150. Additionally, it is possible to utilize separate flow cells for presenting samples to the visible light spectrometer (VIS) 160 and to the Raman spectrometer 170.

The pH probe 180 may be selected from a variety of commercially available sources known to those skilled in the art. In addition to providing a signal which is responsive to the pH of the plating solution, the pH probe 180 in an exemplary embodiment of the present invention provides a temperature signal responsive to the temperature of the sample of the plating solution. The temperature signal may be employed to correct for variations in the pH measurement which occur as a result of varying sample temperature by methods known to skilled artisans. Signals from the visible light spectrometer (VIS) 160, the Raman spectrometer 170, and the pH probe 180 are used for calculating replenishment values for the process chemicals according to methods that will be explained in detail below.

Figure 2:
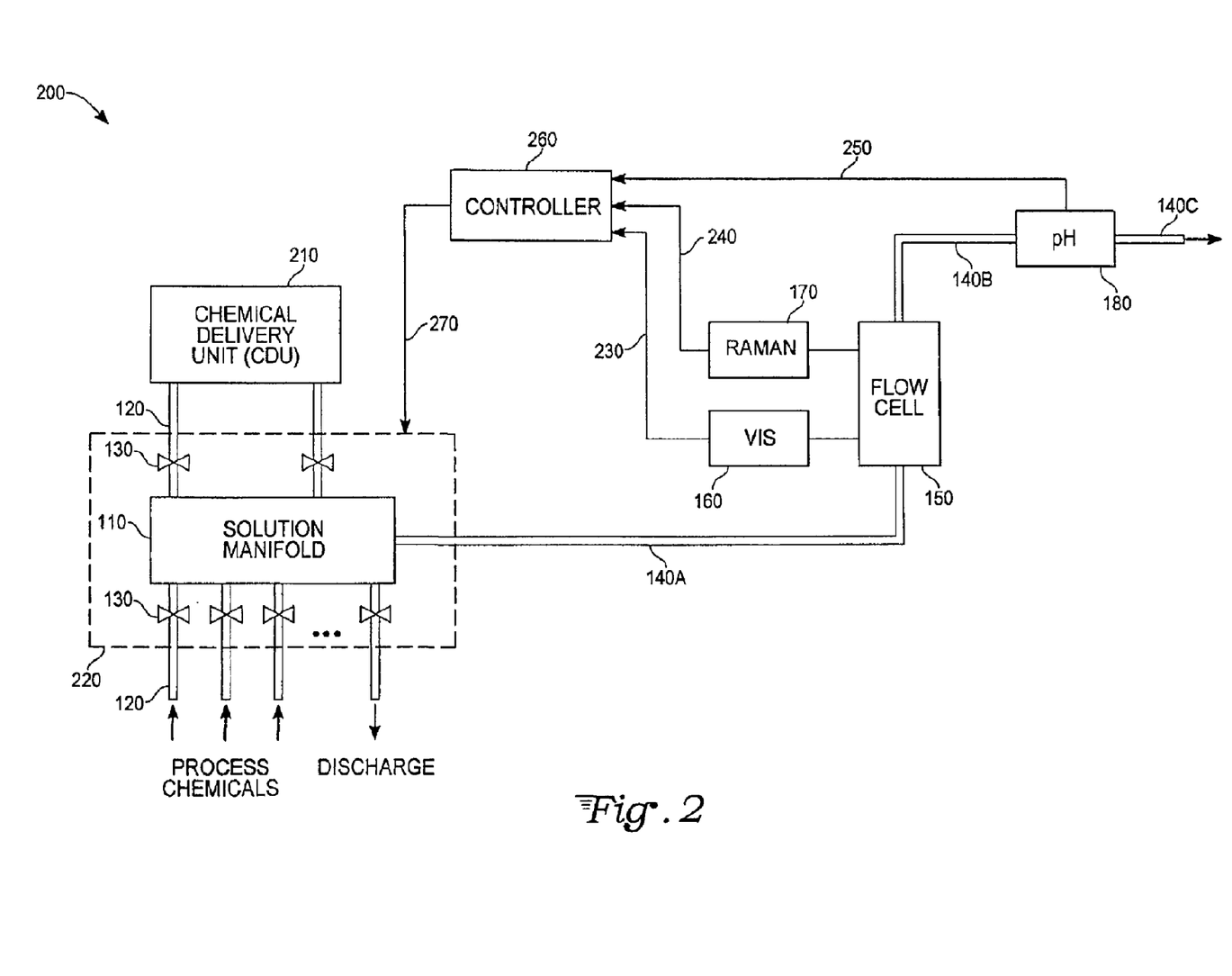
FIG. 2 is an exemplary block diagram of an electroless plating system which utilizes the present invention.
Figure 3A:
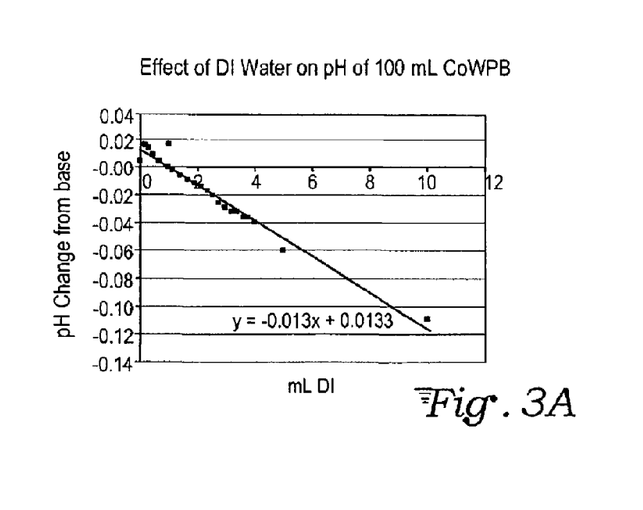
FIG. 3A is a graphical representation of titration response data showing a change in pH as a result of adding deionized (DI) water to 100 milliliter (mL) of electroless CoWPB solution.
Figure 3B:
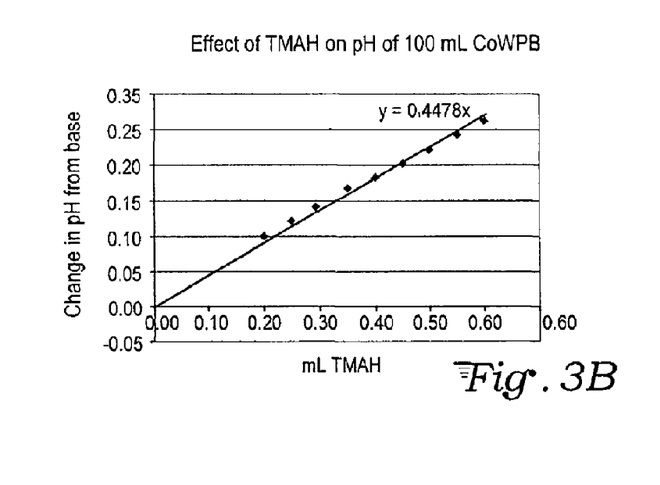
FIG. 3B is a graphical representation of titration response data showing a change in pH as a result of adding a solution of tetramethyl ammonium hydroxide (TMAH) to a 100 milliliter (mL) of electroless CoWPB solution.
Figure 3C:
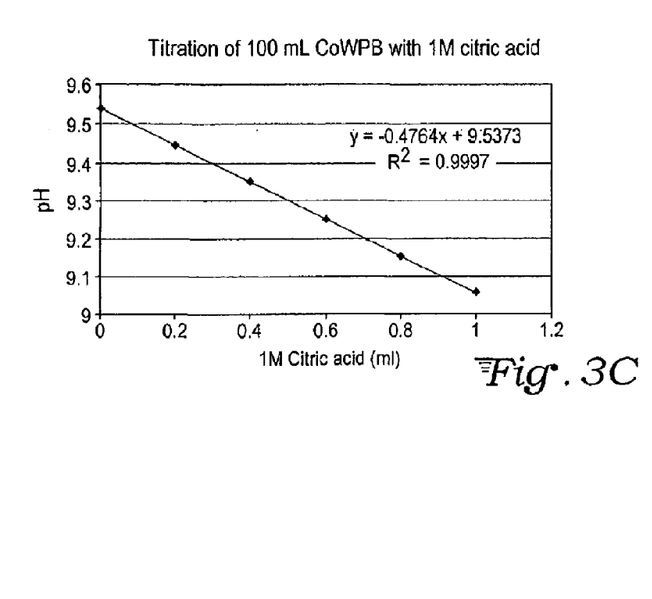
FIG. 3C is a graphical representation of titration response data showing a resulting solution pH as a result of adding a solution of one Molar (1M) solution of citric acid to a 100 milliliter (mL) of electroless CoWPB solution.
Figure 3D:
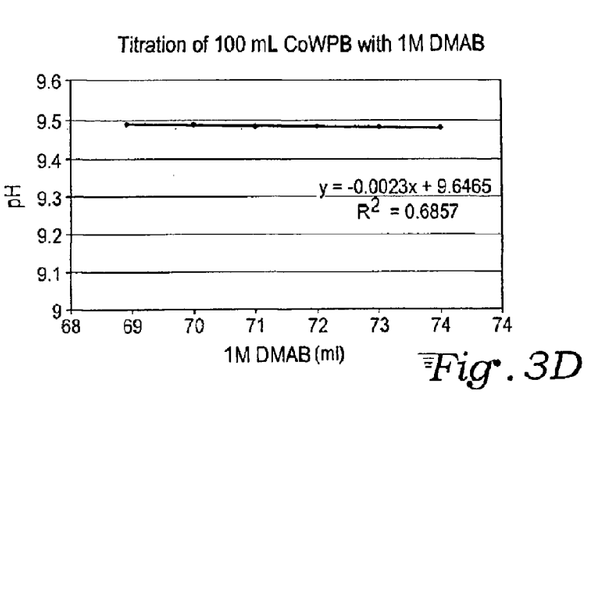
FIG. 3D is a graphical representation of titration response data showing a resulting solution pH as a result of adding a solution of one Molar (1M) solution of dimethylamine borane (DMAB) to a 100 milliliter (mL) of electroless CoWPB solution.

Attention is now directed to FIG. 2, an exemplary embodiment of an electroless plating system 200 according to the present invention. The electroless plating system 200 comprises a chemical delivery unit 210 having a plating solution. The chemical delivery unit 210 is coupled by at least one process solution tube 120 having a throttling valve 130 to the solution manifold 110. In a further embodiment, the chemical delivery unit 210 is coupled by two process solution tubes 120 to the solution manifold 110 to enable a first process solution tube 120 to act as a source for removing a plating solution sample from the chemical delivery unit 210 and to enable a second process solution tube 120 to act as a return for a portion of the plating solution sample and for process chemical admission to the chemical delivery unit 210, as indicated by arrows on the figure. Process chemicals are admitted to the solution manifold 110 through a plurality of process solution tubes 120 as indicated. An additional process solution tube 120 may be employed for the discharge of a portion of the plating solution as indicated. Collectively, the solution manifold 110, the process solution tubes 120, and their associated throttling valves 130 comprise a chemical control system 220.

The first sample tube 140A, the second sample tube 140B, the third sample tube 140C, the flow cell 150, the visible light spectrometer (VIS) 160, the Raman spectrometer 170, and the pH probe 180 shown in FIG. 2 are configured and function analogously as described in reference to FIG. 1, above. An output signal from the visible light spectrometer (VIS) 160 on a VIS signal line 230, responsive to a metal ion concentration in the plating solution sample, couples the visible light spectrometer (VIS) 160 to a controller 260. An output signal from the Raman spectrometer 170 on a Raman signal line 240, responsive to a dimethylamine borane (DMAB) concentration in the plating solution sample, couples the Raman spectrometer 170 to the controller 260. An output signal from the pH probe 180 on a pH output signal line 250, responsive to the pH of the plating solution sample, couples the pH probe 180 to the controller 260. A chemical control signal bus 270 couples the controller 260 to the chemical control system 220.

The controller 260 utilizes the visible light spectrometer (VIS) output signal, the Raman spectrometer output signal, and the pH probe output signal to compute any additions of the process chemicals and discharge of the plating solution to maintain the desired plating solution composition, by methods to be explained below. The controller 260 sends a plurality of control signals by means of the chemical control signal bus 270 to the chemical control system 220 to open and close the plurality of throttling valves 130, thereby performing desired process chemical additions and plating bath discharges. Skilled artisans will recognize that a variety of well-known methods are available to configure the chemical control system 220, the controller 260, and the chemical control signal bus 270.

For example, the chemical control system 220 may utilize pneumatically operated throttling valves, solenoid valves, or other means for varying the flow of fluids. The chemical control system 220 may also incorporate means for measuring fluid parameters such as volumetric or mass flow rates or total fluid volumes. The controller 260 may comprise a personal computer (PC), a programmable logic controller (PLC), a field programmable gate array (FPGA), or other programmable electronic device. The chemical control signal bus 270 may be a series of discrete control wires, or may operate using any of a plurality of well-known serial and parallel data transfer protocols such as Ethernet, CAN, RS-232, and wireless variations thereof. Additionally, the controller 260 may include means for recording data or for providing data to an output device such as a monitor or printer (not shown).

Methods for Plating Solution Control

Exemplary methods for establishing and maintaining the concentration of the chemical components comprising the plating solution within desirable limits will now be described. In the discussions to follow, two general types of computations will be introduced, replenishment computations and dosing computations.

Replenishment computations refer to an addition of one or more chemical solutions to produce a plating bath in the chemical delivery unit (CDU) meeting a set of target values. Dosing computations refer to an addition of one or more chemical solutions to adjust the plating bath composition when the plating bath drifts from the target values. Conceptually, replenishment is employed to create or add to a plating bath while dosing compensates for the consumption of chemical species lost during a plating process. A goal of the replenishment and dosing computations is to give an accurate plating bath composition with a minimal number of calculations, thus avoiding trial-and-error iterations which may allow the plating process to go out of control.

To further facilitate the discussions below, several parameters will be introduced; these are summarized in Table I, below.

TABLE I

| Parameter | Simplified Formula | Parameter Description |
|---|---|---|
| $V_{CDU, orig}$ | A | Original CDU solution volume |
| $C_{DMAB, CDU}$ | B | Original CDU DMAB concentration |
| $V_{CMS}$ | C | Replenishment volume from CMS |
| $A_{CDU, orig}$ | D | Original CDU absorbance |
| $C_{DMAB, supply}$ | E | DMAB concentration (applicable to dosing and replenishment) |
| $C'_{DMAB, CDU}$ | F | Target CDU DMAB concentration |
| $A'_{CDU}$ | G | Target CDU absorbance |
| $A_{CMS}$ | H | CMS absorbance |
| $pH_{CDU, orig}$ | I | Original CDU pH |
| $pH'_{CDU}$ | J | Target CDU pH |
| $V_{CMS, repl.}$ | | Replenishment CMS (chemical makeup solution) volume |
| $V_{CMS, dose}$ | | Dosing CMS (chemical makeup solution) volume |
| $V_{DMAB, repl.}$ | | Replenishment DMAB volume |
| $V_{DMAB, dose}$ | | Dosing DMAB volume |
| $V_{pH, adj., repl.}$ | | Replenishment pH adjuster volume |
| $V_{pH, adj., dose}$ | | Dosing pH adjuster volume |
| $V_{DI, repl.}$ | | Replenishment deionized (DI) water volume |
| $V_{DI, dose}$ | | Dosing deionized (DI) water volume |
| $V_{CDU}$ | | Target solution volume in CDU |
| $V_{CDU, add}$ | | Minimum CDU solution volume; (must add additional solution to CDU if reached) |

In Table I, the abbreviation CDU refers to a chemical delivery unit, and the abbreviation CMS refers a chemical makeup solution having a target composition for a plating bath. In the exemplary embodiment, the chemical makeup solution is the source for metal ions. Further the subscripts "dose" and "repl." are employed to clarify the volume and use of a particular solution in a dosing or replenishment context. (In this exemplary embodiment, dosing and replenishment solution volumes of each chemical originate from a single source, and therefore have the same concentrations. Thus, for example, the concentration of dimethylamine borane solution, $C_{DMAB, repl.}$, is applicable to both dosing and replenishment computations.

A plating bath for the electroless deposition of cobalt tungsten phosphide (CoWP) comprises five chemical solutions: electroless CoWPB solution as a source for metal ions, tetramethyl ammonium hydroxide (TMAH) as a pH adjuster, citric acid as a complexing agent and pH adjuster, dimethylamine borane (DMAB) as a reducing agent, and deionized (DI) water. (In the discussions to follow below, the chemical solutions will be referred to by the abbreviations as defined above.) The influence of each of these chemical solutions on the pH of the plating bath is important to the computation of the relative volumes of the chemicals needed for dosing and replenishment.

Figure 4:
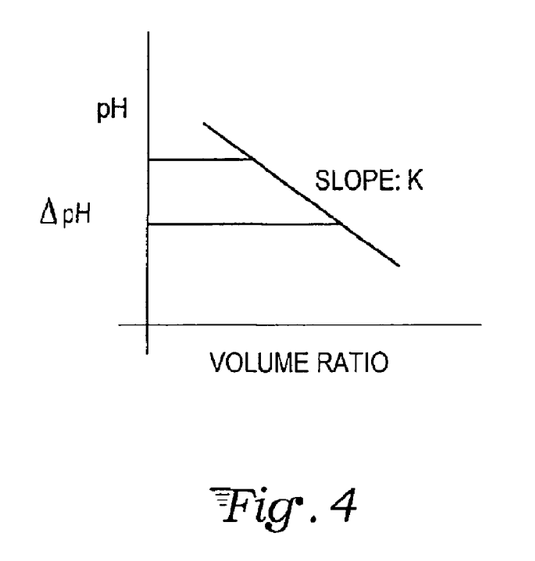
FIG. 4 is a graphical representation of a generic response for a chemical titration.

FIG. 3 is graphical representation of the effects of DI water, TMAH, citric acid, and DMAB on the pH of a solution of electroless CoWPB solution (containing cobalt, tungsten, phosphorous, and boron ions), as determined by the method of chemical titration, known to skilled artisans. With reference to FIG. 4, a generic titration graph, a change in pH, represented by $\Delta$ pH, can be related to a change in the volume ratio of a solution by a linear function having a slope K. Following the example of FIG. 4, the influence each of the chemical solutions TMAH, citric acid, DMAB, and DI on the pH of a solution bath can be expressed by the following formulae:

$$\Delta pH_{CMS} = \frac{V_{CMS}}{V_{CDU,orig} + V_{DMAB} + V_{pH,adj.} + V_{DI}} K_{CMS} \quad (1)$$

$$\Delta pH_{DI} = \frac{V_{DI}}{V_{CDU,orig} + V_{DMAB} + V_{pH,adj.} + V_{CMS}} K_{DI} \quad (2)$$

$$\Delta pH_{DMAB} = \frac{V_{DMAB,repl}}{V_{CDU,orig} + V_{pH,adj.} + V_{CMS} + V_{DI}} K_{DMAB} \quad (3)$$

$$\Delta pH_{pH,adj.} = \frac{V_{pH,adj.}}{V_{CDU,orig} + V_{CMS} + V_{DMAB} + V_{DI}} K_{pH,adj.} \quad (4)$$

In formulae (1)-(4), the values $\Delta pH_{CMS}$, $\Delta pH_{DI}$, $\Delta pH_{DMAB}$, and $\Delta pH_{pH,adj}$, represent the changes in a solution pH resulting from the additions of CMS, DI, DMAB, and pH adjuster solutions, respectively. The volumes of these solution additions are, respectively, $V_{CMS}$, $V_{DI}$, $V_{DMAB}$, and $V_{pH,adj.}$, and are applicable to both dosing and replenishment contexts. The values $K_{DI}$, $K_{DMAB}$, and $K_{pH,adj.}$ are the slopes of the titration response plots, e.g., $K_{DI}$, $K_{pH,adj.}$, and $K_{DMAB}$ may be ascertained from FIGS. 3A, 3B, and 3D respectively. Similar titration plots may be derived for other chemicals commonly employed in plating processes (e.g., CMS) by methods known to those skilled in the art.

The following formulae relate target values for the plating bath properties to the volumes, concentrations, pH, and absorbances of the plating bath chemicals:

$$C'_{DMAB,CDU} = \frac{V_{CDU,orig}C_{DMAB,CDU} + V_{DMAB}C_{DMAB}}{V_{CDU,orig} + V_{pH,adj.} + V_{DMAB} + V_{CMS} + V_{DI}} \quad (5)$$

$$A'_{CDU} = \frac{V_{CDU,orig}A_{CDU,orig} + V_{CMS}A_{CMS}}{V_{CDU,orig} + V_{pH,adj.} + V_{DMAB} + V_{CMS} + V_{DI}} \quad (6)$$

$$pH'_{CDU} = pH_{CDU,orig} + \Delta pH_{DMAB} + \Delta pH_{pH,adj.} + \Delta pH_{CMS} + \Delta pH_{DI} \quad (7)$$

$$V'_{CDU} = V_{CDU,orig} + V_{CMS} + V_{pH,adj.} + V_{DMAB} + V_{DI} \quad (8)$$

where $C'_{DMAB,CDU}$ represents the target concentration for DMAB in the solution in the chemical delivery unit (CDU), $A'_{CDU}$ represents the target absorbance for the solution in the CDU and pH'$_{CDU}$ represents the target pH for the solution in the CDU. The value V'$_{CDU}$ represents a desired volume of solution in the CDU after all additions are made. Since the CDU has a finite volume, it is necessary to perform all computations so as to achieve a volume of solution which does not exceed the CDU capacity. If the computed additions to the CDU exceed its capacity, a portion of any existing solution in the CDU may be drained so as to achieve the desired volume V'$_{CDU}$ after the additions are complete.

Depending upon the condition of the plating bath solution in the CDU, the method for computing the dosing and replenishment volumes is changed. In particular, three cases, each having a different method of calculation will now be described:

Case i: VIS Absorbance of the solution in the CDU is high: compute V$_{DI,dose}$, V$_{DMAB,dose}$, and V$_{pH,adj.,dose}$
  Case ii: VIS Absorbance of the solution in the CDU is low: compute V$_{CMS}$, V$_{DMAB,dose}$, V$_{pH,adj.,dose}$
  Case iii: DMAB concentration in the CDU is high: compute V$_{CMS}$, V$_{DI,dose}$, V$_{pH,adj.,dose}$ In practice, the dosing and replenishment calculations are performed for all three cases; once the computations are complete, the actual values used for dosing and replenishment are selected from a comparison of the three sets of results. Comparison of the results will show that only one calculation method produces non-negative values for all dosing volumes. The other two methods of calculation will produce one or more negative results for the dosing additions. In selecting from the three sets of results, those resulting in negative volumes are rejected, and the result yielding all positive dosing volumes is chosen for control. Thus, the appropriate computation for any given set of process conditions is easily identified. For each case above, a two-part procedure is employed for the dosing and replenishment volume computations:

1. Calculate dosing volumes (i.e., determine the chemical volumes needed to adjust the solution in the CDU to target values for DMAB concentration, absorbance, and pH)
  2. Calculate replenish volumes if the dosing solution volume is less than the difference between normal and add values in the CDU, using the replenishment solution to make up the difference, i.e., so as to satisfy the formula:

$$V_{dosing} + V_{replenish} = V_{CDU,norm} - V_{CDU,add} \quad (9)$$

where: V$_{dosing}$ is the volume of dosing solution added, the dosing solution comprising V$_{CMS,dose}$, V$_{DI,dose}$, V$_{DMAB,dose}$, and V$_{pH,adj.,dose}$; V$_{replenish}$ is the volume of replenishment solution added, the replenishment solution comprising V$_{DMAB,repl.}$, V$_{CMS,repl}$, V$_{DI,repl}$, and V$_{pH,adj.,repl.}$; V$_{CDU,norm}$ is the target solution volume in the CDU; and V$_{CDU,add}$ is the minimum solution volume in the CDU.

Case i: Dosing when VIS Absorbance in CDU is High

Figure 5:
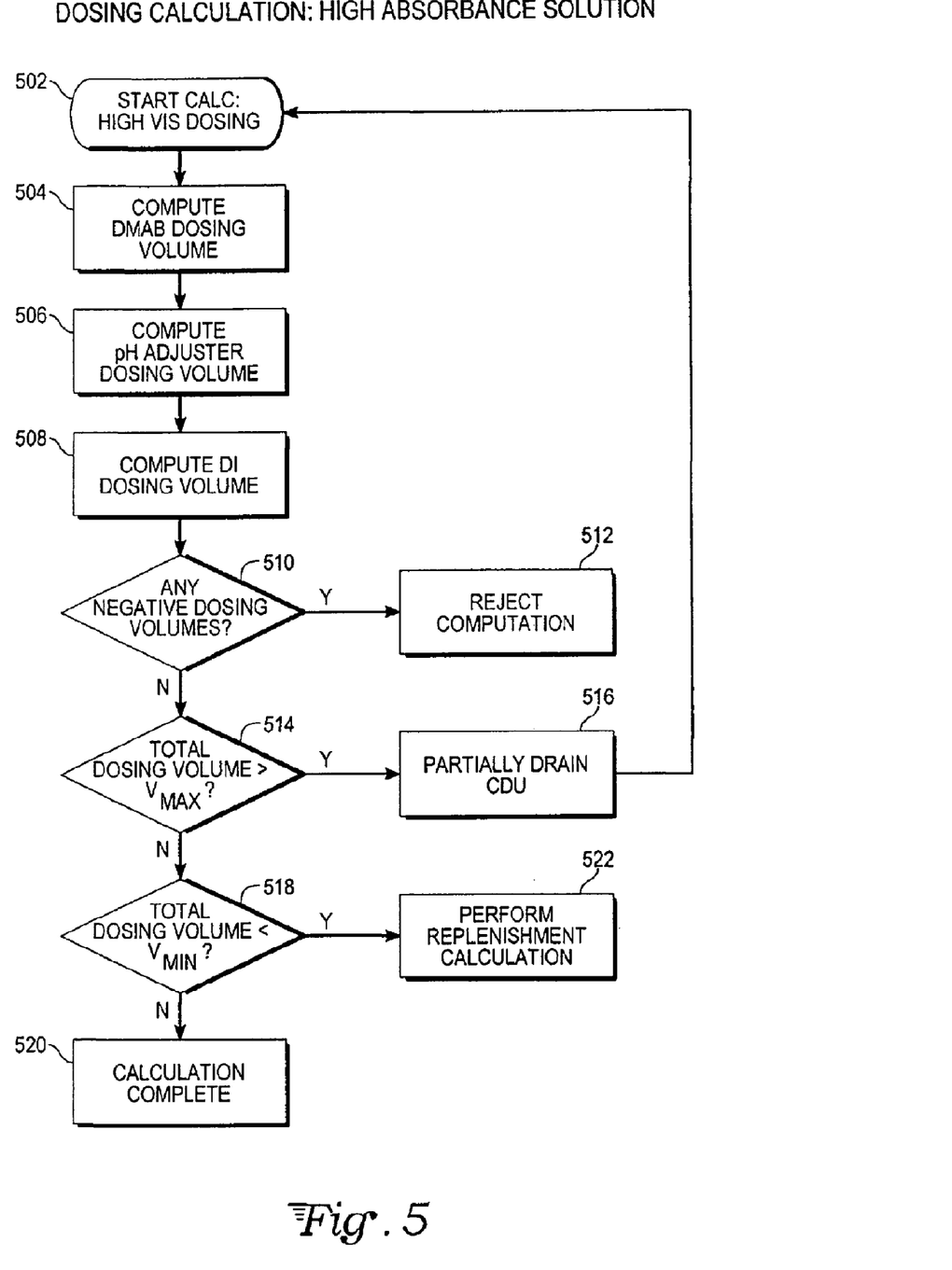
FIG. 5 illustrates an exemplary flowchart for a solution dosing calculation when the absorbance of a solution in a chemical delivery unit (CDU) has a high value.

With reference to FIG. 5, a flowchart for a dosing calculation when the absorbance of a solution in a chemical delivery unit (CDU) is high begins with a high VIS dosing start block 502 for the dosing calculation. For this case, high absorbance is approximately equal to or greater than a value of one (A$_{CDU,orig}$≥~1). A first DMAB dosing volume block 504 computes a dosing volume V$_{DMAB,dose}$ according to the formula:

$$V_{DMAB,dose} = \frac{F(AD+CH) - GBA}{GE} \quad (10)$$

-continued $$= \frac{C'_{DMAB,CDU}(V_{CDU,orig}A_{CDU,orig} + V_{CMS}A_{CMS}) - A'_{CDU}C_{DMAB,CDU}V_{CDU,orig}}{A'_{CDU}C_{DMAB,repl.}}$$

The dosing volume V$_{DMAB,dose}$ is passed next to a first pH adjuster dosing volume block 506 which a computes a pH adjuster dosing volume V$_{pH,dose}$ according to the formula:

$$V_{pH,dose} = \frac{2\beta K_{DI} + \delta K_{DI} + \Omega\beta - \delta K_{pH}}{2(K_{pH} = K_{DI} + \Omega)} \pm \quad (11)$$

$$\frac{\sqrt{(\delta K_{pH} - 2\beta K_{DI} - \delta K_{DI} - \Omega\beta)^2 - 4(K_{pH} + K_{DI} + \Omega)[K_{DI}(\beta\delta + \beta^2) - \Omega(\delta^2 + \delta\beta)]}}{2(K_{pH} + K_{DI} + \Omega)}$$

In formula (11) the following substitutions (using the variables summarized in Table I) have been made to simplify the format of the equation:

$$\alpha = \frac{K_{DMAB}V_{DMAB,dose}}{A+\beta} \quad (12)$$

$$\beta = \frac{A(D-G)}{G} - V_{DMAB,dose} \quad (13)$$

$$\delta = V_{DMAB,dose} + V_{CDU,orig} \quad (14)$$

$$\Omega = J - I - \alpha \quad (15)$$

Since formula (11) contains a computation of a square root, two mathematical solutions of the equation are possible. The result leading to a negative mathematical solution is rejected. If both mathematical solutions are positive, the larger value is chosen. Computation proceeds to a DI dosing volume block 508 which uses the computed values V$_{DMAB,dose}$ and V$_{pH,dose}$ to compute a DI dosing volume V$_{DI,dose}$ according to the formula:

$$V_{DI,dose} = \beta - V_{pH,adj.,dose} \quad (16)$$

$$= \frac{V_{CDU,orig}(A_{CDU,orig} - A'_{CDU})}{A'_{CDU}} -$$

$$V_{DMAB,dose} - V_{pH,adj.,dose}$$

The dosing calculation for Case i now progresses to a first volume check block 510 which checks whether any of the Case i dosing volumes (V$_{DMAB,dose}$, V$_{pH,dose}$, and V$_{DI,dose}$) is negative. If any of the volumes are negative, calculation proceeds to first reject computation block 512 which rejects the computation as invalid. If all dosing volumes are positive, calculation proceeds to a first maximum dosing volume check block 514 which checks whether the addition of the total dosing volume (V$_{DMAB,dose}$+V$_{pH,dose}$+V$_{DI,dose}$) will increase the total CDU solution volume above a value V$_{MAX}$. If V$_{MAX}$ is exceeded, execution proceeds to a first CDU drain block 516 which causes the CDU to partially drain. One method for selecting the amount of solution to be drained from the CDU is to remove a quantity of solution equal to the amount by which the total dosing volume exceeds V$_{MAX}$. Removal of solution from the CDU alters the starting condition for the dosing computation. Therefore, execution is reset to the high VIS dosing start block 502.

If $V_{MAX}$ in the dosing volume check block 514 is not exceeded, the computation proceeds to a first minimum dosing volume check block 518 which checks whether the total dosing volume ($V_{DMAB,dose}+V_{pH,dose}+V_{DI,dose}$) is less than a volume $V_{MIN}$, where $V_{MIN}$ is a volume, which when added to the starting CDU solution volume $V_{CDU,orig}$, exceeds $V_{CDU,ADD}$, the minimum permissible volume of solution in the CDU before additions become necessary. If the total dosing volume is greater than $V_{MIN}$, the calculation proceeds to a first calculation complete block 520. The dosing volumes $V_{DMAB,dose}$, $V_{pH,dose}$, and $V_{DI,dose}$ are ready for use in controlling solution additions to the CDU. If the total dosing volume is less than $V_{MIN}$, additional solution is required by the CDU. Execution proceeds to a first replenishment calculation block 522, which performs a replenishment calculation, by methods to be explained further, below.

Dosing when VIS Absorbance in CDU is Low

Figure 6:
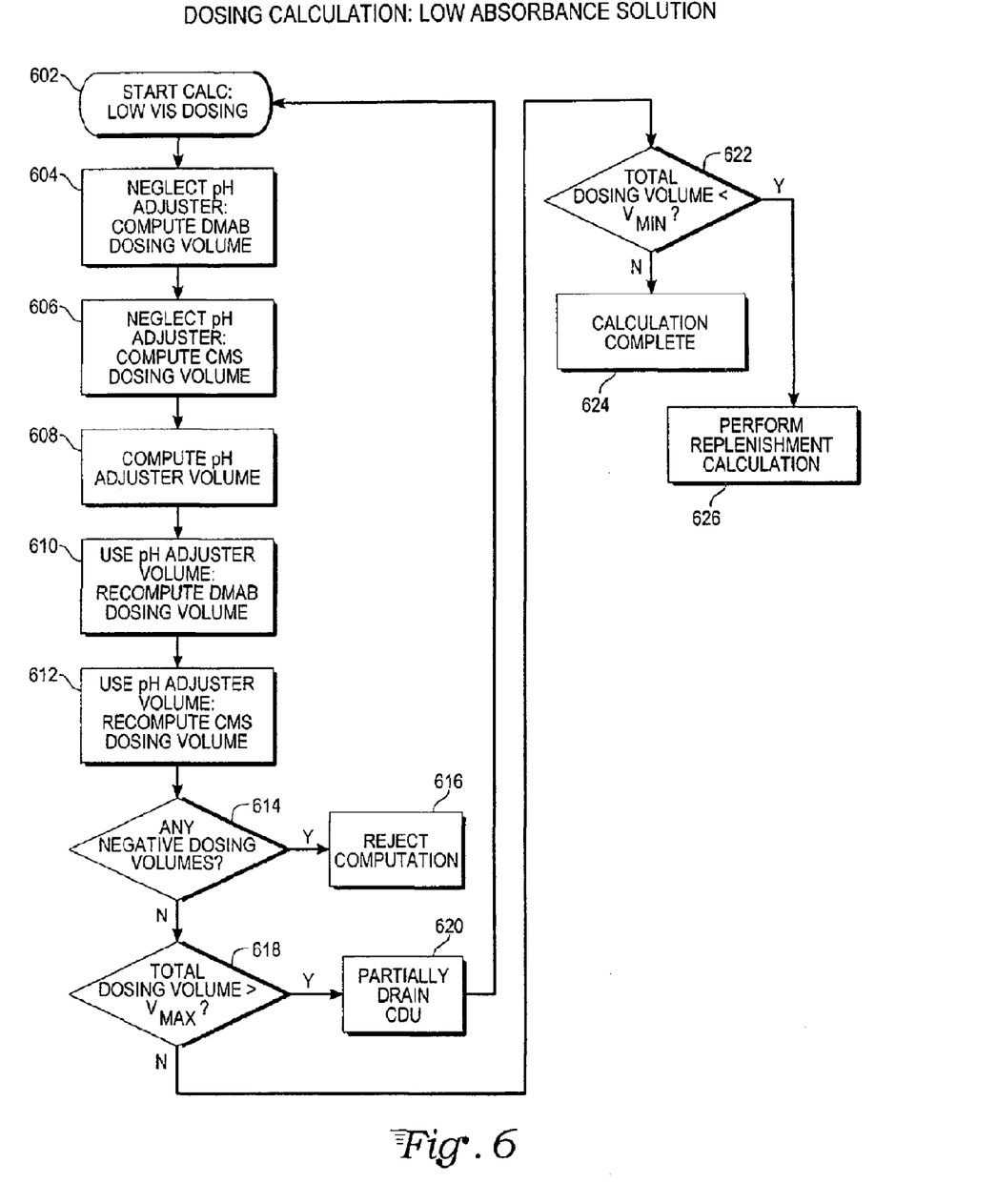
FIG. 6 illustrates an exemplary flowchart for a solution dosing calculation when the absorbance of a solution in a chemical delivery unit has a low value.

With reference to FIG. 6, a flowchart for a dosing calculation when the absorbance of a solution in a chemical delivery unit (CDU) is low begins with a low VIS dosing start block 602 for the dosing calculation. For this case, low absorbance is approximately less than a value of one ($A_{CDU,orig} < \sim 1$). A second DMAB dosing volume block 604 computes a dosing volume $V_{DMAB,dose}$, according to the formula:

$$V_{DMAB,dose} = \frac{C'_{DMAB,CDU}(V_{CDU,orig} + V_{pH,adj} + V_{CMS}) - C_{DMAB,CDU}V_{CDU,orig}}{(C_{DMAB,repl.} - C'_{DMAB,CDU})} \quad (17)$$

In the evaluation of formula (17), the second DMAB dosing volume block 604 makes use of the simplifying assumptions:

$$V_{CDU,orig} + V_{CMS} >> V_{pH,adj} \quad (18)$$

$$V_{CDU,orig} + V_{DMAB,dose} >> V_{pH,adj} \quad (19)$$

Formulae (18) allows the volume of pH adjuster solution to be ignored in formula (17), which is therefore simplified to:

$$V_{DMAB,dose.} = \frac{C'_{DMAB,CDU}(V_{CDU,orig} + V_{CMS}) - C_{DMAB,CDU}V_{CDU,orig}}{C_{DMAB,repl.} - C'_{DMAB,CDU}} \quad (20)$$

Computation progresses to a first CMS dosing volume block 606, which computes a dosing volume $V_{CMS,dose}$ according to the formula:

$$V_{CMS,dose} = \frac{A'_{CDU}(V_{CDU,orig} + V_{pH,adj.} + V_{DMAB,repl.}) - A_{CDU,orig}V_{CDU,orig}}{A_{CMS} - A'_{CDU}} \quad (21)$$

The assumptions of formulae (18) and (19) are applied by the first CMS dosing volume block 606, simplifying the calculation performed by block 606 to the following:

$$V_{CMS,dose} = \frac{A'_{CDU}(V_{CDU,orig} + V_{DMAB,repl.}) - A_{CDU,orig}V_{CDU,orig}}{A_{CMS} - A'_{CDU}} \quad (22)$$

The dosing calculation for Case ii now progresses to a second pH adjuster dosing volume block 608, which uses the values $V_{DMAB,dose}$ and $V_{CMS,dose}$ computed from formulae (20) and (22) respectively to compute the pH adjuster dosing volume $V_{ph,adj,dose}$ based upon the relation:

$$pH'_{CDU} - pH_{CDU,orig} = \frac{V_{CMS}K_{CMS}}{V_{CDU,orig} + V_{DMAB,dose.} + V_{pH,adj.,dose}} + \frac{V_{DMAB}K_{DMAB}}{V_{CDU,orig} + V_{CMS} + V_{pH,adj.,dose}} + \frac{V_{pH,adj.}K_{pH}}{V_{CDU,orig} + V_{CMS} + V_{DMAB,dose}} \quad (23)$$

The volume of pH adjuster in the denominator portions of formula (23) can be neglected, simplifying the expression to:

$$pH'_{CDU} - pH_{CDU,orig} = \frac{V_{CMS}K_{CMS}}{V_{CDU,orig} + V_{DMAB,dose.}} + \frac{V_{DMAB,dose}K_{DMAB}}{V_{CDU,orig} + V_{CMS}} + \frac{V_{pH,adj.,dose}K_{pH}}{V_{CDU,orig} + V_{CMS} + V_{DMAB,dose.}} \quad (24)$$

After appropriate rearrangement, formula (24) can be solved for $V_{ph,adj,dose}$. Once the dosing volume of pH adjuster is determined, the dosing volumes for DMAB and CMS are re-evaluated to improve the accuracy of the calculation. The value for $V_{ph,adj,dose}$ is passes to a first recomputed DMAB dosing volume block 610 which re-computes and updates the DMAB dosing volume $V_{DMAB,dose}$ according to formula (17). In this case, the pH adjuster dosing volume is utilized in the computation and is not ignored. Computation proceeds to a first recomputed CMS dosing volume block 612 which re-computes and updates the CMS dosing volume $V_{CMS,dose}$ according to formula (23). Again, $V_{ph,adj,dose}$, the pH adjuster dosing volume, is utilized in the computation and is not ignored.

The dosing calculation for Case ii now progresses to a second volume check block 614 which determines whether any of the Case ii dosing volumes ($V_{DMAB,dose}$, $V_{pH,dose}$, and $V_{DI,dose}$) are negative. If any of the volumes are negative, calculation proceeds to second reject computation block 616 which rejects the computation as invalid. If all dosing volumes are positive, calculation proceeds to a second maximum dosing volume check block 618 which checks whether the addition of the total dosing volume ($V_{DMAB,dose}+V_{pH,dose}+V_{DI,dose}$) will increase the total CDU solution volume above the value $V_{MAX}$. If $V_{MAX}$ is exceeded, execution proceeds to a second CDU drain block 620 which causes the CDU to partially drain. One method for selecting the amount of solution to be drained from the CDU is to remove a quantity of solution equal to the amount by which the total dosing volume exceeds $V_{MAX}$. Removal of solution from the CDU alters the starting condition for the dosing computation. Therefore, execution is reset to the low VIS dosing start block 602.

If $V_{MAX}$ in the second maximum dosing volume check block 618 is not exceeded, the computation proceeds to a second minimum dosing volume check block 622 which checks whether the total dosing volume ($V_{DMAB,dose}+V_{pH,dose}+V_{DI,dose}$) is less than the volume $V_{MIN}$. If the total dosing volume is greater than $V_{MIN}$, the calculation proceeds to second calculation complete block 624. The dosing volumes $V_{DMAB,dose}$, $V_{pH,dose}$, and $V_{DI,dose}$ are ready for use in controlling solution additions to the CDU. If the total dosing volume is less than $V_{MIN}$, additional solution is required by CDU. Execution proceeds to a second replenishment calculation block 626, which performs a replenishment calculation, by methods to be explained further, below.

Dosing when DMAB Concentration in CDU is High

Figure 7:
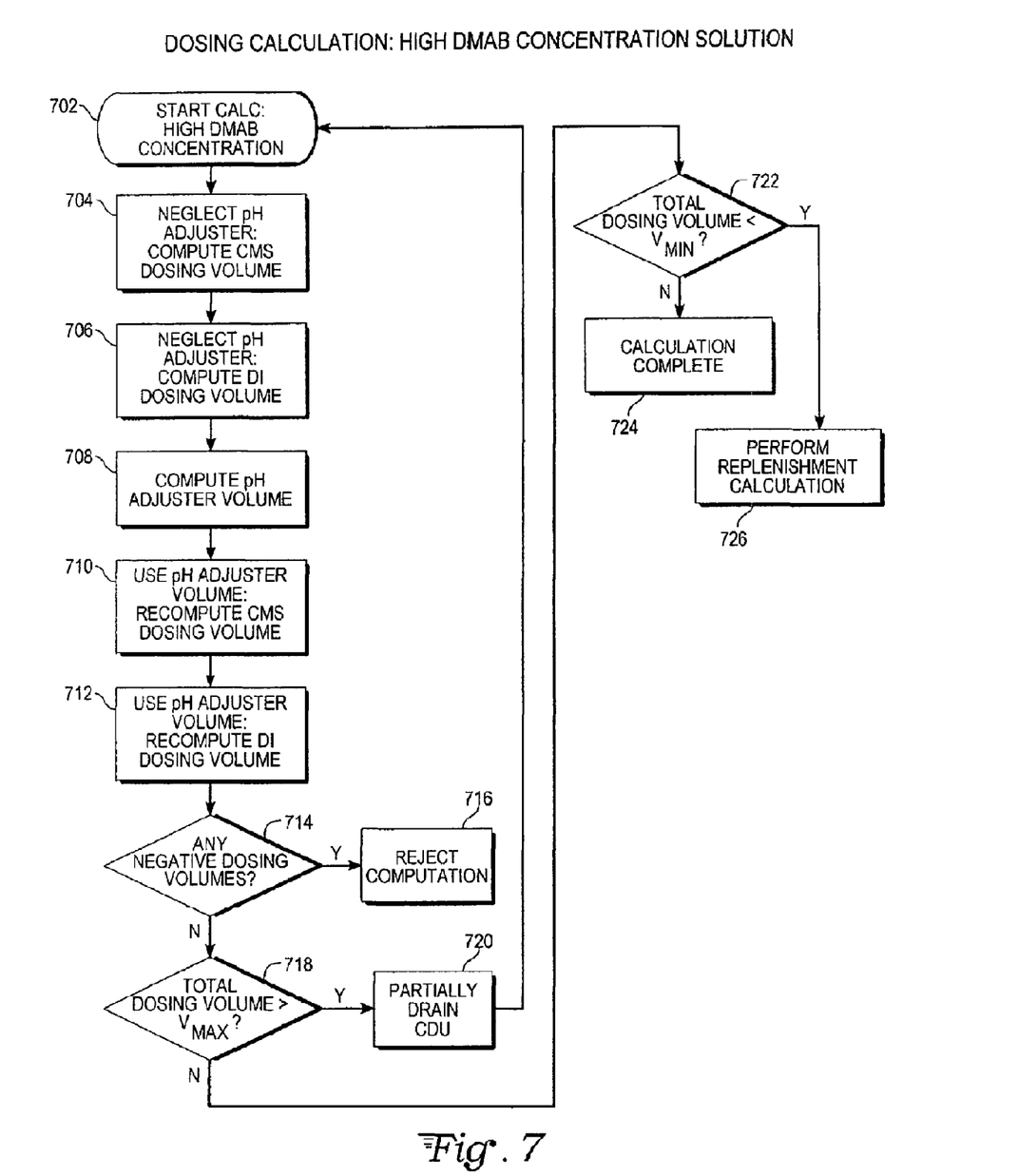
FIG. 7 illustrates an exemplary flowchart for a solution dosing calculation when a solution in a chemical delivery unit has a high dimethylamine borane (DMAB) concentration.

With reference to FIG. 7, a flowchart for a dosing calculation when the DMAB concentration of a solution in a chemical delivery unit (CDU) is high begins with a high DMAB dosing start block 702 for the dosing calculation. For this case, a high DMAB concentration is approximately greater than a value of 45 milli-Molar ($C_{DMAB,orig}>\sim 0.45$ mM). Starting with an assumption that $V_{DMAB,dose}=0$, second CMS dosing volume block 704 computes a dosing volume $V_{CMS,dose}$, according to the formula:

$$A'_{CDU} = \frac{V_{CDU,orig}A_{CDU,orig} + V_{CMS}A_{CMS}}{V_{CDU,orig} + V_{pH,adj.} + V_{CMS} + V_{DI}} \quad (25)$$

which after rearranging gives:

$$V_{CMS,dose} = \frac{V_{CDU}(A'_{CDU}C_{DMAB,CDU} - A_{CDU}C'_{DMAB,CDU})}{C'_{DMAB,CDU}A_{CMS}} \quad (26)$$

Computation progresses to a first DI dosing volume block 706, which computes a dosing volume $V_{DI,dose}$ beginning with the formula:

$$C'_{DMAB,CDU} = \frac{V_{CDU,orig}C_{DMAB,CDU}}{V_{CDU,orig} + V_{pH,adj.} + V_{CMS,dose} + V_{DI,dose}} \quad (27)$$

using the assumption:

$$V_{CDU}+V_{CMS,dose}+V_{DI,dose} >> V_{pH,adj.} \quad (28)$$

By rearranging formula (27) with the assumption of formula (28), and applying the value of $V_{CMD,dose}$ computed by block 704 the volume $V_{DI,dose}$ is computed as:

$$V_{DI,dose} = \frac{V_{CDU,orig}C_{DMAB,CDU} - C'_{DMAB,CDU}(V_{CDU,orig} + V_{CMS,dose})}{C'_{DMAB,CDU}} \quad (29)$$

The dosing calculation for Case iii now progresses to a second pH adjuster dosing volume block 708, which uses the values $V_{CMS,dose}$ and $V_{DI,dose}$ computed from formulae (26) and (29) respectively to compute the pH adjuster dosing volume $V_{ph,adj,dose}$ based upon the relation:

$$pH'_{CDU} - pH_{CDU,orig} = \frac{V_{CMS}K_{CMS}}{V_{CDU,orig} + V_{DI,dose} + V_{pH,adj,dose}} + \quad (30)$$

$$\frac{V_{DI}K_{DI}}{V_{CDU,orig} + V_{CMS} + V_{pH,adj,dose}} +$$

$$\frac{V_{pH,adj.}K_{pH}}{V_{CDU,orig} + V_{CMS} + V_{DI,dose}}$$

The volume of pH adjuster in the denominator portions of formula (30) can be neglected, simplifying the expression to:

$$pH'_{CDU} - pH_{CDU,orig} = \frac{V_{CMS}K_{CMS}}{V_{CDU,orig} + V_{DI,dose}} + \quad (31)$$

$$\frac{V_{DI,dose}K_{DI}}{V_{CDU,orig} + V_{CS,dose}} +$$

$$\frac{V_{pH,adj,dose}K_{pH}}{V_{CDU,orig} + V_{CMS,dose} + V_{DI,dose}}$$

After appropriate rearrangement, formula (31) can be solved for $V_{ph,adj,dose}$. Once the dosing volume of pH adjuster is determined, the dosing volumes for DMAB and CMS are re-evaluated to improve the accuracy of the calculation. The value for $V_{ph,adj,dose}$ is passed to a second recomputed CMS dosing volume block 710 which re-computes and updates the CMS dosing volume $V_{CMS,dose}$ according to formula (26). In this case, the pH adjuster dosing volume is utilized in the computation and is not ignored. Computation proceeds to a first recomputed DI dosing volume block 712 which re-computes and updates the DI dosing volume $V_{DI,dose}$ according to formula (29). Again, the pH adjuster dosing volume is utilized in the computation and is not ignored.

The dosing calculation for Case iii now progresses to a third volume check block 714 which checks whether any of the Case iii dosing volumes ($V_{DMAB,dose}$, $V_{pH,dose}$, and $V_{DI,dose}$) are negative. If any of the volumes are negative, calculation proceeds to a third reject computation block 716 which rejects the computation as invalid. If all dosing volumes are positive, calculation proceeds to a third maximum dosing volume check block 718 which checks whether the addition of the total dosing volume ($V_{DMAB,dose}+V_{pH,dose}+V_{DI,dose}$) will increase the total CDU solution volume above the value $V_{MAX}$. If $V_{MAX}$ is exceeded, execution proceeds to a third CDU drain block 720 which causes the CDU to partially drain. One method for selecting the amount of solution to be drained from the CDU is to remove a quantity of solution equal to the amount by which the total dosing volume exceeds $V_{MAX}$. Removal of solution from the CDU alters the starting condition for the dosing computation. Therefore, execution is reset to the high DMAB dosing start block 702.

If $V_{MAX}$ in the third maximum dosing volume check block 718 is not exceeded, the computation proceeds to a third minimum dosing volume check block 722 which checks whether the total dosing volume ($V_{DMAB,dose}+V_{pH,dose}+V_{DI,dose}$) is less than the volume $V_{MIN}$. If the total dosing volume is greater than $V_{MIN}$, the calculation proceeds to a third calculation complete block 724. The dosing volumes $V_{DMAB,dose}$, $V_{pH,dose}$, and $V_{DI,dose}$ are ready for use in controlling solution additions to the CDU. If the total dosing volume is less than $V_{MIN}$, additional solution is required by CDU. Execution proceeds to a third replenishment calculation block 726, which performs a replenishment calculation, by methods to be explained further, below.

Replenishment Calculations

In this exemplary embodiment of the present invention, if any of the dosing calculations for Cases i, ii, or iii (described above) require a corresponding replenishment computation, the replenishment volumes are determined by the following method, described with reference to FIG. 8.

Figure 8:
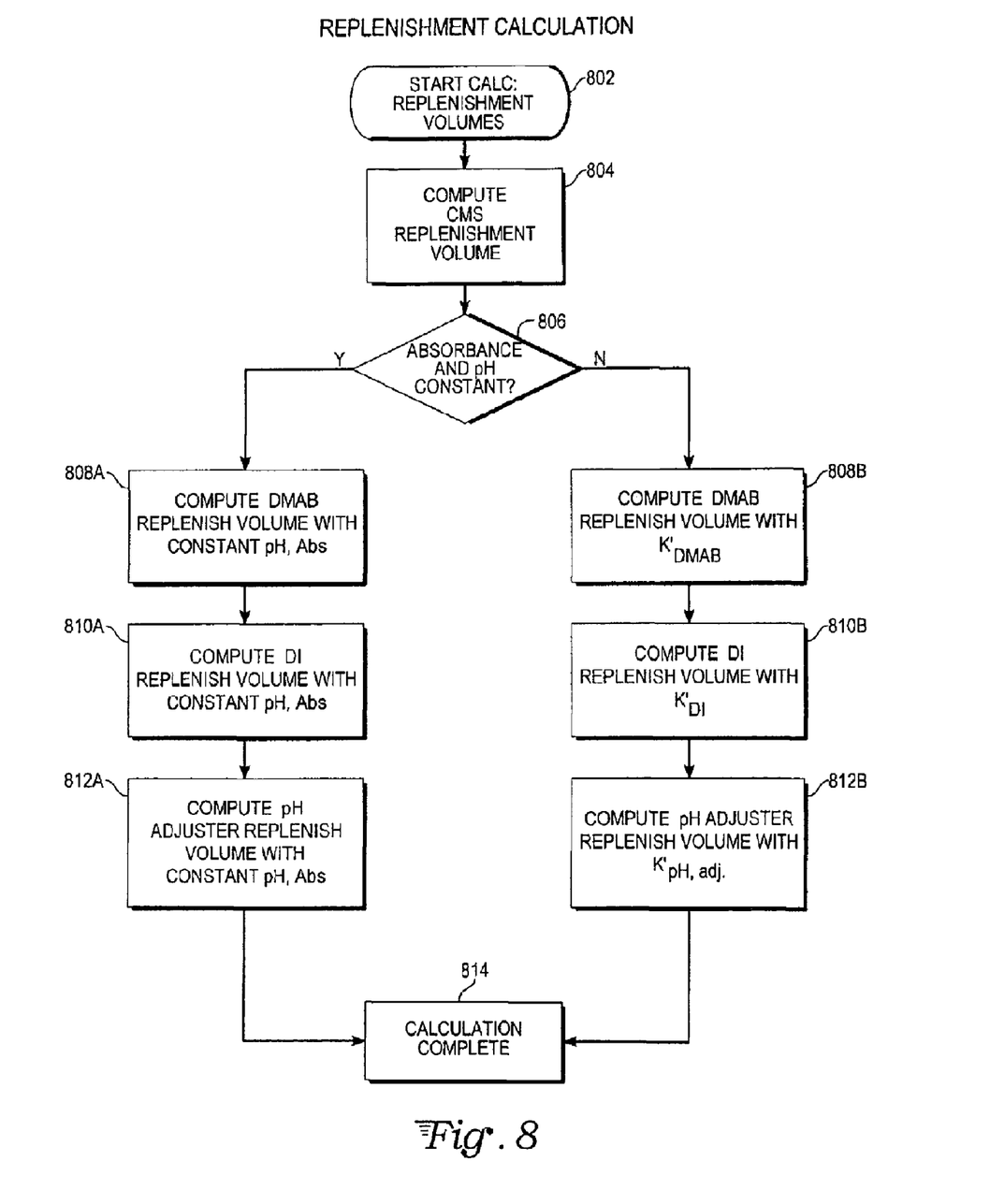
FIG. 8 illustrates an exemplary flowchart for a solution replenishment calculation for a chemical delivery unit.

In FIG. 8, computation begins at a replenishment computation start block 802, an entry point for the calculations to follow and progresses to a CMS replenishment volume block 804 which computes a CMS replenishment volume $V_{CMS,repl}$ according to the formula:

$$V_{CMS,repl} = \frac{A'_{CDU} V_{repl.}}{A_{CMS}} \quad (32)$$

where $V_{repl}$ is the total volume of replenishment solution determined from the computations described above in the dosing calculations. Formula (32) estimates the volume of CMS replenishment solution which must additionally satisfy the relations:

$$A'_{CDU} = \frac{V_{CMS,repl} A_{CMS}}{V_{pH,adj.,repl} + V_{DMAB,repl.} + V_{CMS,repl} + V_{DI,repl}} \quad (33)$$

and $$V_{repl.} + V_{pH,adj.} + V_{DMAB,repl.} + V_{CMS} + V_{DI} \quad (34)$$

The replenishment solution computation progresses to absorbance and pH case selection block 806 which selects a further path for the replenishment computation according to whether the CMS absorbance and pH are anticipated to be relatively constant or varying as the other plating solution components are added.

Case where CMS Absorbance and pH are Relatively Constant

If the CMS absorbance and pH are relatively constant, the replenishment calculation proceeds to a DMAB replenish volume for constant parameter block 808A, a DI replenish volume for constant parameters block 810A, and a pH adjuster replenish volume for constant parameters block 812A. These blocks compute the replenishment volumes for DMAB, DI, and pH adjuster replenishment solutions to satisfy the relation:

$$V_{repl} = V_{CMS,repl}(1 + \alpha_{pH,adj.,repl} + \alpha_{DI,repl} + \alpha_{DMAB,repl.}) \quad (35)$$

where:

$$\alpha_{pH,adj,repl} V_{CMS,repl} = V_{pH,adj,repl} \quad (36a)$$

$$\alpha_{DMAB,repl} V_{CMS,repl} = V_{DMAB,repl} \quad (36b)$$

$$\alpha_{DI,repl} V_{CMS,repl} = V_{DI,repl} \quad (36c)$$

In the actual implementation, blocks 804, 808A, 810A, and 812A may be executed in a different sequence or may be solved simultaneously by methods known to skilled artisans. For example, commercial software for the implementation of spreadsheet computations frequently incorporates an iterative solver which can be employed to find solutions which simultaneously satisfy a plurality of mathematical requirements and constraints.

Once the replenishment volumes $V_{CMS,repl}$, $V_{pH,adj.,repl}$, $V_{CMS,repl}$, and $V_{DMAB,repl}$ are computed to satisfy the total replenishment volume $V_{repl}$, execution progresses to a replenishment calculation complete block 814, and the replenishment volumes are ready for use in controlling solution additions to the CDU.

Case where CMS Absorbance and pH are Varying

If the CMS absorbance and pH are varying, the replenishment calculation proceeds to a DMAB replenish volume with a titration slope block 808B, a DI replenish volume with titration slope block 810B, a pH adjuster replenish volume with a titration slope block 812B. These blocks compute replenishment volumes for DMAB, DI, and pH adjuster replenishment solutions to satisfy the relation:

$$C'_{DMAB,CDU} = \frac{V_{DMAB,repl.} C_{DMAB,repl.}}{V_{pH,adj.,repl} + V_{DMAB,repl.} + V_{CMS,repl} + V_{DI,repl}} \quad (37)$$

The DMAB replenish volume with titration slope block 808B computes the DMAB replenishment volume from the formula:

$$V_{DMAB,repl} = \frac{C'_{DMAB,CDU} V_{repl.}}{C_{DMAB,repl.}} \quad (38)$$

The following relations are then used by blocks 810B and 812B to compute the replenishment volumes $V_{DI,repl}$ and $V_{pH,adj.,repl}$:

$$pH'_{CDU} = \quad (39)$$
$$pH_{CMS} + \frac{V_{DI} K'_{DI}}{V_{repl.} - V_{DI}} + \frac{V_{pH,adj.} K'_{pH}}{V_{repl.} + V_{pH,adj.}} + \frac{V_{DMAB,repl.} K'_{DMAB,repl.}}{V_{repl.} + V_{DMAB,repl.}}$$

$$V_{repl.} = V_{pH,adj.} + V_{DMAB,repl.} + V_{CMS} + V_{DI} \quad (40)$$

In formula (39), the varying pH and absorbance of the chemical makeup solution (CMS) is included by means of the titration slopes:

$$K'_{DI} = \frac{A_{CMS} K_{DI}}{A'_{CDU}} \quad (41a)$$

$$K'_{DMAB} = \frac{A_{CMS} K_{DMAB}}{A'_{CDU}} \quad (41b)$$

$$K'_{pH,adj.} = \frac{A_{CMS} K_{pH,adj.}}{A'_{CDU}} \quad (41C)$$

These titration slopes have been discussed above with reference to FIGS. 3 and 4. In the actual implementation, blocks 804, 808B, 810B, and 812B may be executed in a different sequence or may be solved simultaneously by methods known to skilled artisans.

Once the replenishment volumes $V_{CMS,repl}$, $V_{pH,adj.,repl}$, $V_{CMS,repl}$, and $V_{DMAB,repl}$ are computed to satisfy the total replenishment volume $V_{repl}$, execution progresses to a replenishment calculation complete block 814, and the replenishment volumes are ready for use in controlling solution additions to the CDU.

In the foregoing specification, the present invention has been described with reference to specific embodiments thereof. It will, however, be evident to a skilled artisan that various modifications and changes can be made thereto without departing from the broader spirit and scope of the present invention as set forth in the appended claims. For example, although the apparatus and method of the present invention is described primarily in reference to the electroless deposition of cobalt tungsten phosphide, skilled artisans will appreciate that the present invention may also be applied to the electroless deposition of other materials, to analysis and control of electroplating solutions, and to other chemical processes where it is desirable to determine the concentrations of both organic and metallic components simultaneously present in a solution. For example, a specific embodiment of the present invention may be beneficially applied to electroless plating of nickel phosphide (NiP). In this specific embodiment, hypophosphite would be employed in place of DMAB as a reducing agent, and a concentration of nickel ions in solution would be measured by absorption, using a wavelength in which a visible light spectrometer (VIS) or absorption meter was responsive to the nickel ions. The specification and drawings are, accordingly, to be regarded in an illustrative rather than a restrictive sense.

What is claimed is:

1. A system used in electroless plating of metallic compounds, the system comprising:
   a visible light spectrometer configured for visible light measurement technique to measure an absorbance of the plating solution, the absorbance of the plating solution being an indication of the concentration of different metal ions in the plating solution;
   a Raman spectrometer configured for Raman measurement technique to measure a concentration of a reducing agent in the plating solution;
   a pH probe configured to measure a pH level of the plating solution;
   a sampling system comprising a flow cell, configured to measure components of a plating solution, the plating solution having a reducing agent, a pH adjusting agent, and at least one metal in solution, the sampling system further configured to divert a portion of the plating solution to the Raman spectrometer to measure a concentration of the reducing agent, the sampling system also to divert a portion of the plating solution to the visible light spectrometer (VIS) to measure a concentration of different metal ions in solution, the sampling system further to divert a portion of the plating solution to the pH probe to measure a pH level of the plating solution, wherein the Raman spectrometer and the visible light spectrometer are operatively connected to the flow cell in parallel and the flow cell is fluidly connected to the pH probe; and
   a control system connected to the visible light spectrometer, the Raman spectrometer, and the pH probe, the control system being configured to utilize the measurements of the visible light spectrometer, the Raman spectrometer, and the pH probe to determine dosing additions of a chemical makeup solution, the reducing agent, a pH adjusting solution, and deionized (DI) water to the plating solution, the dosing additions functioning to replace plating solution components diminished by a plating process, and to determine replenishment additions of the chemical makeup solution, the reducing agent, the pH adjusting solution, and deionized (DI) water to the plating solution, the replenishment additions functioning to maintain a target volume of the plating solution and to replenish any of the reducing agent, the pH adjusting agent, and at least one metal in solution.

2. The system of claim 1, wherein the Raman spectrometer comprises a 785 nanometer wavelength light source and the visible light spectrometer (VIS) comprises a green light source having a wavelength between approximately 490 nanometers and approximately 540 nanometers.

3. The system of claim 1, wherein the pH probe incorporates a temperature sensor to enable determination of and correction for variations in pH measurements as a function of temperature.

4. The system of claim 1, further comprising a solution manifold, wherein the control system, is further configured to control the solution manifold for adding any of the reducing agent, the pH adjusting agent, and any of the different metal ions in solution if their respective concentrations in the plating solution are below a setpoint value, and by the addition of deionized (DI) water if any of their respective concentrations is above a setpoint value.

5. A system for controlling the composition of a plating solution, the system comprising:
   a flow cell;
   a visible light spectrometer configured for visible light measurement technique to measure an absorbance of the plating solution in the flow cell, the absorbance of the plating solution being an indication of the concentration of at least one metal in the plating solution;
   a Raman spectrometer configured for Raman measurement technique to measure a concentration of a reducing agent in the plating solution in the flow cell;
   a pH probe configured to measure a pH level of the plating solution, wherein the Raman spectrometer and the visible light spectrometer are operatively connected to the flow cell in parallel and the flow cell is fluidly connected to the pH probe; and
   a controller controllably connected to the pH probe, the Raman spectrometer, and the visible light spectrometer, the controller being configured to utilize the measurements of the visible light spectrometer, the Raman spectrometer, and the pH probe to determine dosing additions of a chemical makeup solution, the reducing agent, a pH adjusting solution, and deionized (DI) water to the plating solution, the dosing additions to replace plating solution components diminished by a plating process, the controller further configured to determine replenishment additions of the chemical makeup solution, the reducing agent, the pH adjusting solution, and deionized (DI) water to the plating solution, the replenishment additions to maintain a target volume of the plating solution.

6. The system of claim 5, further comprising a temperature sensor.

7. The system of claim 5, wherein the chemical makeup solution is electroless CoWPB solution, the reducing agent is dimethylamine borane (DMAB), and the pH adjusting solution is any of tetramethyl ammonium hydroxide (TMAH) and citric acid.

8. A system for controlling the composition of an electroless plating solution, the system comprising:
   a visible light spectrometer configured for visible light measurement technique to measure an absorbance of the plating solution, the absorbance of the plating solution being an indication of the concentration of different metal ions in the plating solution;
   a Raman spectrometer configured for Raman measurement technique to measure a concentration of a reducing agent in the plating solution;
   a pH probe configured to measure a pH level of the plating solution;
   means for diverting a sample portion of the electroless plating solution to the Raman spectrometer to measure a concentration of a reducing agent in the sample portion, to the visible spectrometer to measure an absorbance of the sample portion, and to the pH probe to measure a pH value of the sample portion, a flow cell connected to the means for diverting the sample portion, wherein the Raman spectrometer and the visible light spectrometer are operatively connected to the flow cell in parallel and the flow cell is fluidly connected to the pH probe;

means for computing being programmed to compute a dosing solution volume, controllably connected to the pH probe, the Raman spectrometer, and the visible light spectrometer, the dosing solution comprising portions of the reducing agent, deionized (DI) water, a pH adjusting solution, and a chemical makeup solution, the dosing solution volume acting to maintain a target composition of the electroless plating solution;

means for computing being further programmed to compute a replenishment solution volume, the replenishment solution comprising portions of the reducing agent, deionized (DI) water, a pH adjusting solution, and a chemical makeup solution, the replenishment solution volume acting to maintain a target volume of the electroless plating solution utilizing the measurements of the visible light spectrometer, the Raman spectrometer, and the pH probe to determine dosing additions of a chemical makeup solution, the reducing agent, a pH adjusting solution, and deionized (DI) water to the plating solution, the dosing additions functioning to replace plating solution components diminished by a plating process, and to determine replenishment additions of the chemical makeup solution, the reducing agent, the pH adjusting solution, and deionized (DI) water to the plating solution, the replenishment additions functioning to maintain a target volume of the plating solution; and means for adding any of the dosing solution volume and the replenishment solution volume to the electroless plating solution.

9. The system of claim 8 wherein the means for computing being further programmed to compute a dosing solution volume is programmed to select a method for computing the dosing solution volume on the basis of the absorbance of the sample portion and the concentration of the reducing agent in the sample portion.

10. The system of claim 8, wherein the means for computing being further programmed to compute a replenishment solution volume is programmed to select a method for computing the replenishment solution volume on the basis of a pH change and an absorbance change in the chemical makeup solution based on a determination the chemical makeup solution is subjected to additions of any of deionized (DI) water, the pH adjusting solution, and the reducing agent.

11. The system of claim 8, wherein the reducing agent is dimethylamine borane (DMAB) and the pH adjusting solution is any of tetramethyl ammonium hydroxide (TMAH) and citric acid.

12. A system used to measure a plating solution, the system comprising:
a flow cell;
a solution sampling apparatus having a solution manifold including:
a plurality of process solution tubes including throttling valves with at least one of the process solution tubes configured to be coupled to the plating solution; and
a first sample tube coupled to the solution manifold and to the flow cell, the first sample tube configured to convey a sample of the plating solution from the solution manifold to the flow cell; and
a visible light spectrometer configured for visible light measurement technique coupled to the flow cell and having a light source configured to measure an absorbance of the plating solution in the flow cell;
a Raman spectrometer configured for Raman measurement technique coupled to the flow cell and having a light source configured to measure a concentration of a component of the plating solution in the flow cell; and
a second sample tube coupled to a flow cell and to a pH probe, the second sample tube configured to convey the sample of the plating solution from the flow cell, to the pH probe, the pH probe configured to measure a pH value of the plating solution, wherein the Ramen spectrometer and the visible light spectrometer are operatively connected to the flow cell in parallel and the flow cell is fluidly connected to the pH probe.

13. The system, as recited in claim 1, wherein the Raman spectrometer comprises an infrared optical source, so that the Raman spectrometer operates in the infrared portion of the spectrum, and wherein the visible light spectrometer comprises a visible light source, so that the visible light spectrometer operates in the visible portion of the spectrum.

14. The system, as recited in claim 1, wherein the Raman spectrometer comprises an infrared optical source, so that the Raman spectrometer operates in the infrared portion of the spectrum, and wherein the visible light spectrometer comprises a green light source having a wavelength between approximately 490 nanometers and approximately 540 nanometers, so that the visible light spectrometer operates in the visible portion of the spectrum.

15. The system, as recited in claim 5, wherein the Raman spectrometer comprises an infrared optical source, so that the Raman spectrometer operates in the infrared portion of the spectrum, and wherein the visible light spectrometer comprises a visible light source so that the visible light spectrometer operates in the visible portion of the spectrum.

16. The system, as recited in claim 5, wherein the Raman spectrometer comprises an infrared optical source, so that the Raman spectrometer operates in the infrared portion of the spectrum, and wherein the visible light spectrometer comprises a green light source having a wavelength between approximately 490 nanometers and approximately 540 nanometers, so that the visible light spectrometer operates in the visible portion of the spectrum.

17. The system of claim 5, wherein the Raman spectrometer comprises a 785 nanometer wavelength light source and the visible light spectrometer (VIS) comprises a green light source having a wavelength between approximately 490 nanometers and approximately 540 nanometers.

18. The system, as recited in claim 8, wherein the Raman spectrometer comprises an infrared optical source, so that the Raman spectrometer operates in the infrared portion of the spectrum, and wherein the visible light spectrometer comprises a green light source having a wavelength between approximately 490 nanometers and approximately 540 nanometers, so that the visible light spectrometer operates in the visible portion of the spectrum.

19. The system of claim 8, wherein the Raman spectrometer comprises a 785 nanometer wavelength light source and the visible light spectrometer (VIS) comprises a green light source having a wavelength between approximately 490 nanometers and approximately 540 nanometers.

20. The system, as recited in claim 8, wherein the Raman spectrometer comprises an infrared optical source, so that the Raman spectrometer operates in the infrared portion of the spectrum, and wherein the visible light spectrometer comprises a visible light source so that the visible light spectrometer operates in the visible portion of the spectrum.

* * * * *